(12) United States Patent
Tseng et al.

(10) Patent No.: US 11,399,964 B2
(45) Date of Patent: Aug. 2, 2022

(54) OPERATING INSTRUMENT AND METHOD FOR SPINAL IMPLANT

(71) Applicant: WILTROM CO., LTD., Zhubei (TW)

(72) Inventors: Chang-Ho Tseng, Taipei (TW);
Meng-Yuan Tsai, Taipei (TW);
Chieh-Feng Lu, Zhubei (TW);
Yen-Ting Tseng, Zhubei (TW);
Wan-Chun Chen, Zhubei (TW);
Huang-Chi Chen, Zhubei (TW)

(73) Assignee: WILTROM CO., LTD., Zhubei (TW)

( * ) Notice: Subject to any disclaimer, the term of this patent is extended or adjusted under 35 U.S.C. 154(b) by 0 days.

(21) Appl. No.: 17/090,515

(22) Filed: Nov. 5, 2020

(65) Prior Publication Data

US 2021/0128319 A1 May 6, 2021

(30) Foreign Application Priority Data

Nov. 6, 2019 (TW) .................................. 108140303

(51) Int. Cl.
*A61F 2/46* (2006.01)
*A61F 2/44* (2006.01)
*A61F 2/30* (2006.01)

(52) U.S. Cl.
CPC .............. *A61F 2/4611* (2013.01); *A61F 2/44* (2013.01); *A61F 2002/30579* (2013.01); *A61F 2002/4627* (2013.01); *A61F 2002/4629* (2013.01); *A61F 2002/4638* (2013.01)

(58) Field of Classification Search
CPC ............ A61F 2/4611; A61F 2002/4627; A61F 2002/4629
See application file for complete search history.

(56) References Cited

U.S. PATENT DOCUMENTS

| 10,085,844 B2 | 10/2018 | Perloff et al. |
| 11,253,369 B2 * | 2/2022 | Tseng ................. A61B 17/8816 |
| 11,266,513 B2 * | 3/2022 | Greendyk ............. A61F 2/4611 |
| 2002/0026197 A1 | 2/2002 | Foley et al. |

(Continued)

FOREIGN PATENT DOCUMENTS

| CN | 102274066 B | 8/2015 |
| CN | 103622733 B | 6/2016 |

(Continued)

*Primary Examiner* — Matthew J Lawson
(74) *Attorney, Agent, or Firm* — Muncy, Geissler, Olds & Lowe, P.C.

(57) ABSTRACT

The present disclosure discloses an operating instrument for a spinal implant. The operating instrument includes an extension assembly, a central rod, and an operating handle. The extension assembly includes an outer sleeve, and one end of the outer sleeve is connected with a first part of the spinal implant. The central rod passes through the outer sleeve, and one end of the central rod connects to a second part of the spinal implant. The operating handle includes a fixing element, a rotating element, and a pushing element. The rotating element is sleeved on the outer side of the fixing element. The pushing element connects with the central rod, and the rotating element presses against the pushing element. The rotating element is rotated to cause the pushing element to drive the central rod to move the second part, thereby expanding the spinal implant.

12 Claims, 17 Drawing Sheets

(56) References Cited

U.S. PATENT DOCUMENTS

| | | | |
|---|---|---|---|
| 2013/0053965 A1* | 2/2013 | Metz-Stavenhagen ... | A61F 2/44 623/17.16 |
| 2014/0135780 A1* | 5/2014 | Lee .......................... | A61F 2/44 606/94 |
| 2015/0173808 A1* | 6/2015 | Sack .................. | A61B 17/1671 606/86 A |
| 2015/0272650 A1* | 10/2015 | Dubois .................. | A61F 2/447 606/99 |
| 2017/0258600 A1* | 9/2017 | Tseng ................ | A61B 17/8852 |
| 2019/0167442 A1* | 6/2019 | Scott-Young ......... | A61F 2/4611 |
| 2020/0253619 A1* | 8/2020 | Gregory ............... | A61M 29/00 |

FOREIGN PATENT DOCUMENTS

| | | |
|---|---|---|
| EP | 2730246 A1 | 5/2014 |
| TW | I589266 B | 7/2017 |

* cited by examiner

OPERATING INSTRUMENT AND METHOD FOR SPINAL IMPLANT

BACKGROUND

1. Technical Field

The present disclosure relates to an operating instrument for a spinal implant and a method for operating the operating instrument.

2. Description of the Related Art

The spine is one of the most important components of the human musculoskeletal system. A spinal injury or disorder often has a considerable impact on the patient, causing symptoms such as pain, numbness, weakness, and even incontinence or difficulty in urinating and defecating. The above symptoms are caused by displacements between the vertebral bodies (bone segments), which can compress the nerves or spinal cord. In clinical diagnosis, spinal disorders can be divided into diagnoses such as vertebral compression fractures, disc herniation, spondylolisthesis, spinal stenosis, or degenerative scoliosis, based on the etiology of the condition. When the symptoms are severe, patients often cannot relieve their discomfort through correction and must rely on spinal surgery for restoration treatment.

FIGS. 1A and 1B are schematic diagrams of a spinal implant. For displacements caused by vertebral body collapse and flatness, such as compression fracture of a vertebral body due to osteoporosis, the most effective surgical method at present is to insert and place a spinal implant 9 in a folded state (as shown in FIG. 1A) at the cancellous bone of the vertebral body, and to use an operating instrument to expand the spinal implant to an expanded state (as shown in FIG. 1B), thereby propping up the vertebral body to a certain height such that the bone cement has enough filling space, and then to complete the restoration of the vertebral body after the bone cement has solidified. Specifically, the spinal implant 9 comprises a first part 91, a second part 92, an expansion arm 93, and a supporting arm 94, and all of the above can be integrally formed. Both the first part 91 and the second part 92 are hollow cylinders, wherein the first part 91 and the second part 92 are separated from each other without overlapping and arranged along the same horizontal line (X axis). That is, the first part 91 and the second part 92 are connected through the expansion arm 93 and the supporting arm 94. When the spinal implant 9 is in the folded state, the distance between the first part 91 and the second part 92 is very small, and they may even abut each other. The operating instrument is used for adjusting the distance between the first part 91 and the second part 92 to change the degree of expansion of the spinal implant 9. For example, the first part 91 can be fixed and the second part 92 can be pushed to increase the distance between the first part 91 and the second part 92 to expand the expansion arm 93 and supporting arm 94 outward.

However, if the distance that the second part 92 is pushed is not properly controlled, the expansion arm 93 could protrude to the extent that the expansion arm 93 penetrates the vertebral body and increases the risk of the surgery. Therefore, the expansion of the spinal implant 9 must be carefully controlled; otherwise, there will be medical risks.

At present, there is no available device on the market that can cooperate with the spinal implant 9 and can precisely control the pushed distance of the second part.

SUMMARY

In view of the above-mentioned problems, the main object of the present disclosure is to provide an operating instrument for a spinal implant and an operating method thereof, wherein the operating instrument cooperates with the spinal implant to make it more efficient and easier to adjust the position of the spinal implant and the degree of expansion during spinal surgery.

In order to achieve the above object, the present disclosure provides an operating instrument for a spinal implant. The operating instrument comprises an extension assembly, a central rod, and an operating handle. The extension assembly comprises an outer sleeve, and one end of the outer sleeve has a connecting portion connected with the first part of the spinal implant. The central rod is inserted into the outer sleeve, and one end of the central rod is connected with the second part of the spinal implant. The operating handle comprises a fixing element, a rotating element, and a pushing element. The fixing element has an outer thread. The rotating element has an inner thread, wherein the rotating element is sleeved on the outside of the fixing element, and the inner thread and the outer thread correspond to each other. The pushing element is connected with the central rod, and the rotating element is pressed against the pushing element. The rotating element is rotated so as to cause the pushing element to move along the long axis of the central rod, and the central rod is driven to drive the second part to move, thereby changing the distance between the second part and the first part so as to expand the spinal implant.

According to an embodiment of the present disclosure, the central rod has a first end and a second end opposing each other; the first end is connected with the second part, and the pushing element is connected with the second end.

According to an embodiment of the present disclosure, the pushing element comprises an assembly hole; the second end of the central rod has a fixing part, the assembly hole is in communication with the fixing part, and the operating instrument comprises a retracting element mounted in the assembly hole and engaged with the fixing part of the central rod.

According to an embodiment of the present disclosure, the retracting element is a retracting screw comprising a nut and a screw body; the operating handle comprises a through hole, and the through hole is in communication with the assembly hole; the screw body is inserted into the through hole to be mounted in the assembly hole, and the nut is retained outside of the operating handle.

According to an embodiment of the present disclosure, when the rotating element is reversely rotated to cause the retracting element move in the opposite direction along the long axis of the central rod, the central rod is driven to drive the second part to move in the opposite direction, thereby changing the distance between the second part and the first part for retraction of the spinal implant.

According to an embodiment of the present disclosure, the retracting element further comprises a washer disposed between the rotating element and the nut.

According to an embodiment of the present disclosure, the extension assembly further comprises a joining unit connecting the fixing element with one end of the outer sleeve opposite to the connecting portion.

According to an embodiment of the present disclosure, the operating handle is adjacent to the joining unit, the operating handle has at least one movement marker, and the movement marker is disposed on the side of the operating handle close to the joining unit.

According to an embodiment of the present disclosure, the extension assembly further comprises an indicator, and the indicator indicates the moving distance of the central rod.

According to an embodiment of the present disclosure, the indicator is disposed on the outside of the joining unit and has a tip, the movement marker is disposed on one end of the rotating element adjacent to the joining unit, and the tip extends from the joining unit to the outside of the rotating element.

According to an embodiment of the present disclosure, the operating handle comprises a plurality of the movement markers, and the rotating element is rotated to move the tip to overlap with one of the movement markers.

According to an embodiment of the present disclosure, the extension assembly further comprises a gripping portion connected with the joining unit, and the gripping portion is not parallel to the outer sleeve.

According to an embodiment of the present disclosure, the joining unit has a first accommodating groove, and a portion of the outer sleeve is accommodated in the first accommodating groove; the front end of the fixing element has a pipe, and the pipe is accommodated in the first accommodating groove and sleeved on the outside of the outer sleeve.

According to an embodiment of the present disclosure, the fixing element has a second accommodating groove and is in communication with the outer sleeve, and the second end of the central rod and a portion of the pushing element are accommodated in the second accommodating groove.

In order to achieve the above objects, the present disclosure also provides a method for operating an operating instrument of a spinal implant. The spinal implant comprises a first part and a second part; the operating instrument comprises an extension assembly, a central rod, and an operating handle; the extension assembly comprises an outer sleeve; the operating handle comprises a fixing element, a rotating element, and a pushing element; the fixing element has an outer thread; the rotating element has an inner thread; the rotating element is sleeved on the outside of the fixing element; and the inner thread and the outer thread correspond to each other. The operation method comprises the following steps of: connecting, by a connecting portion of the outer sleeve, the extension assembly with the first part of the spinal implant; inserting the central rod into the outer sleeve; connecting one end of the central rod with the second part of the spinal implant; connecting, by the pushing element, the operating handle with the central rod, and pressing the rotating element against the pushing element; and rotating the rotating element to cause the pushing element to move along the long axis of the central rod so as to drive the central rod to drive the second part to move, thereby changing the distance between the second part and the first part to expand the spinal implant.

According to an embodiment of the present disclosure, the pushing element comprises an assembly hole, the central rod has a fixing part, the assembly hole is in communication with the fixing part, and the operating instrument comprises a retracting element, the operation method further comprising the following steps of mounting the retracting element in the assembly hole, engaging the retracting element with the fixing part of the central rod, and reversely rotating the rotating element so as to cause the retracting element to move in the opposite direction along the long axis of the central rod and to drive the central rod to drive the second part to move in the opposite direction, thereby changing the distance between the second part and the first part to retract the spinal implant.

As described above, in the operating instrument for a spinal implant of the present disclosure, the outer sleeve of the extension assembly is connected with the first part of the spinal implant, and the central rod is inserted into the outer sleeve and connected with the second part of the spinal implant. The operating handle has a fixing element, a rotating element and a pushing element. The inner thread of the rotating element corresponds to the outer thread of the fixing element, the pushing element is connected with the central rod, and the rotating element abuts against the pushing element. The surgeon needs only to rotate the rotating element, and the pushing element can drive the central rod to drive the second part to move, thereby changing the distance between the second part and the first part so as to expand the spinal implant. Therefore, the operating instrument of the present disclosure enables the surgeon to precisely control the moving distance of the second part so as to carefully adjust the degree of expansion of the spinal implant to achieve a better treatment effect.

The mechanism of the operating instrument is suitable for the operating instrument to work with the retracting element to perform the function of retracting the spinal implant. The retracting element can be easily assembled with the operating handle so as to be connected with the central rod and thereby to control the movement of the second part. When the retracting element is assembled, the surgeon needs only to reversely rotate the rotating element to cause the pushing element to drive the central rod to cause the second part to move in the opposite direction, thereby changing the distance between the second part and the first part to retract the spinal implant. In this way, the present disclosure can solve the problems of the spinal implant possibly being implanted improperly and needing to be removed and re-inserted again, or the degree of expansion being too large and needing to be reduced, among other issues.

DETAILED DESCRIPTION OF THE EMBODIMENTS

In order to make the structure and characteristics as well as the effectiveness of the present disclosure further understood and recognized, the detailed description of the present disclosure is provided as follows along with embodiments and accompanying figures.

Figure 1A:
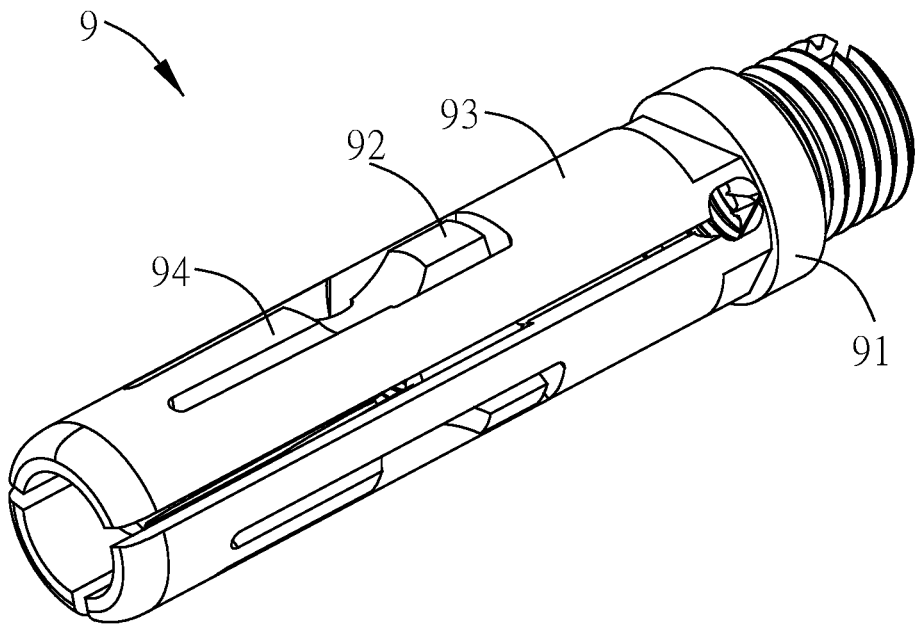
FIGS. 1A and 1B are schematic diagrams of a spinal implant.
Figure 1B:
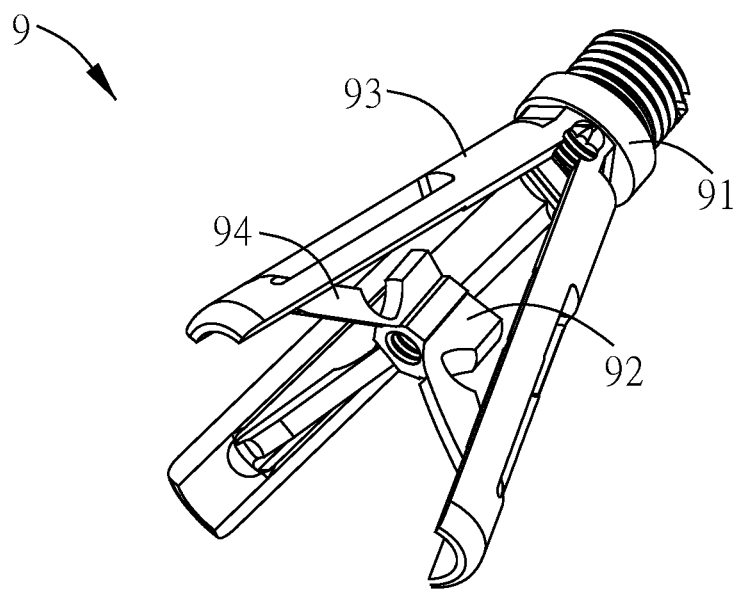
Figure 2:
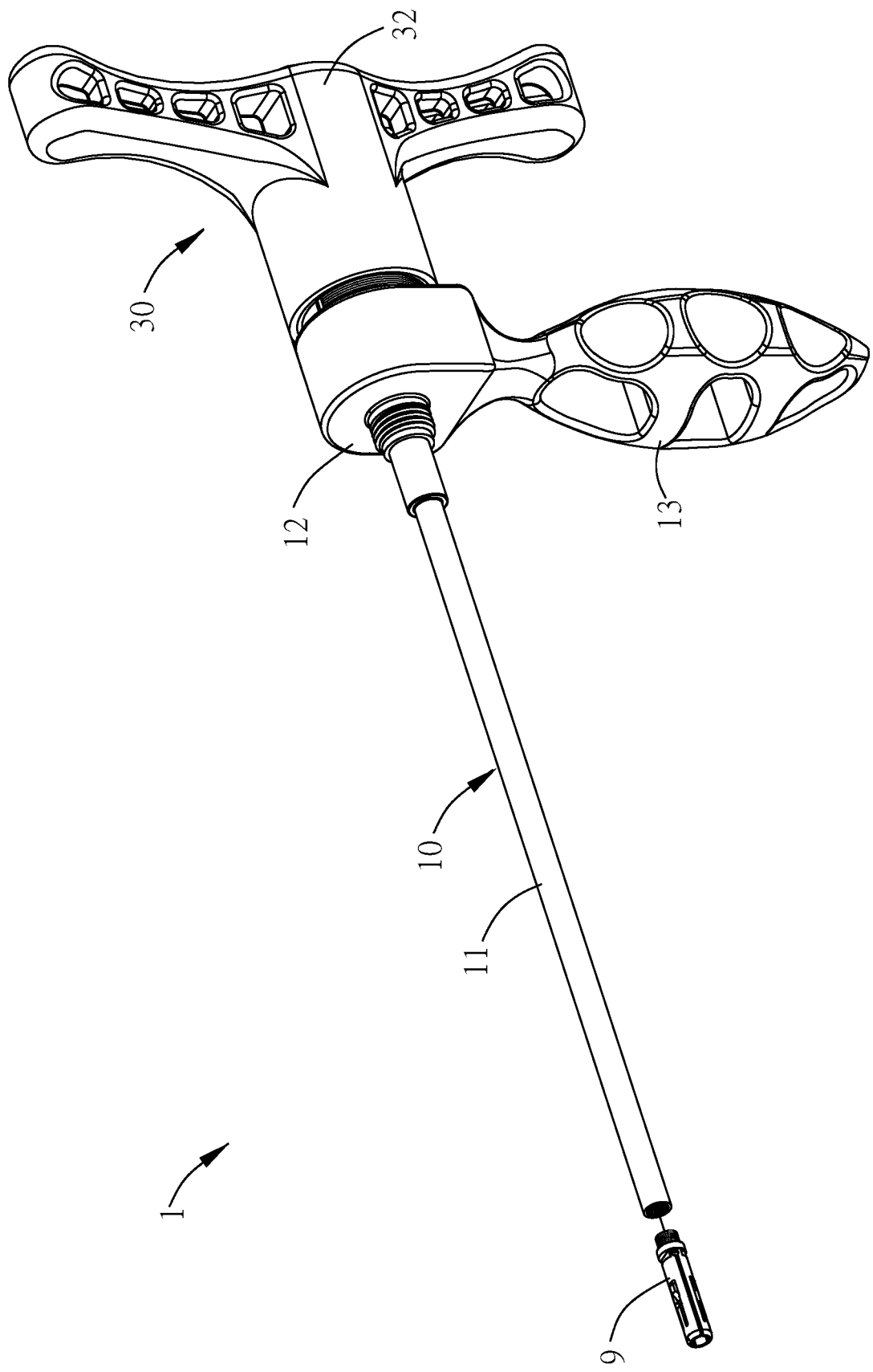
FIG. 2 is a schematic diagram of an embodiment of the operating instrument for a spinal implant of the present disclosure.
Figure 3A:
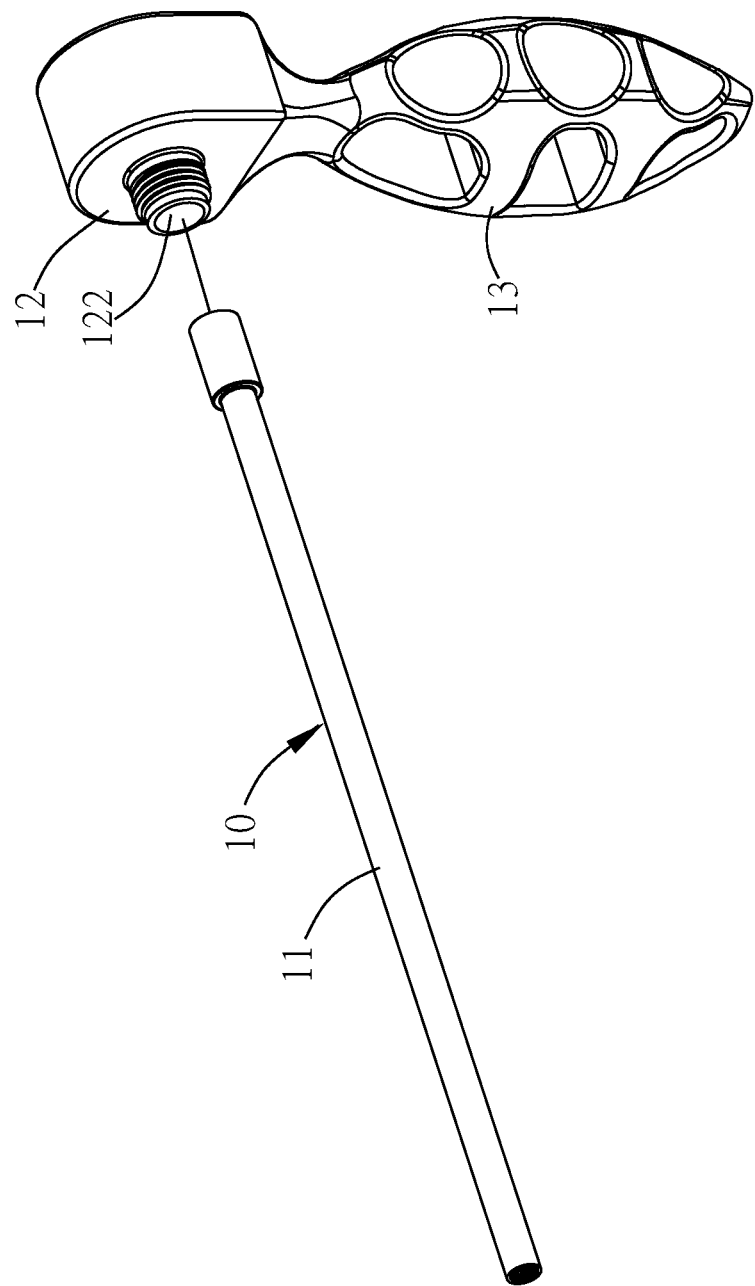
FIG. 3A is an exploded schematic diagram of the extension assembly shown in FIG. 2.
Figure 3B:
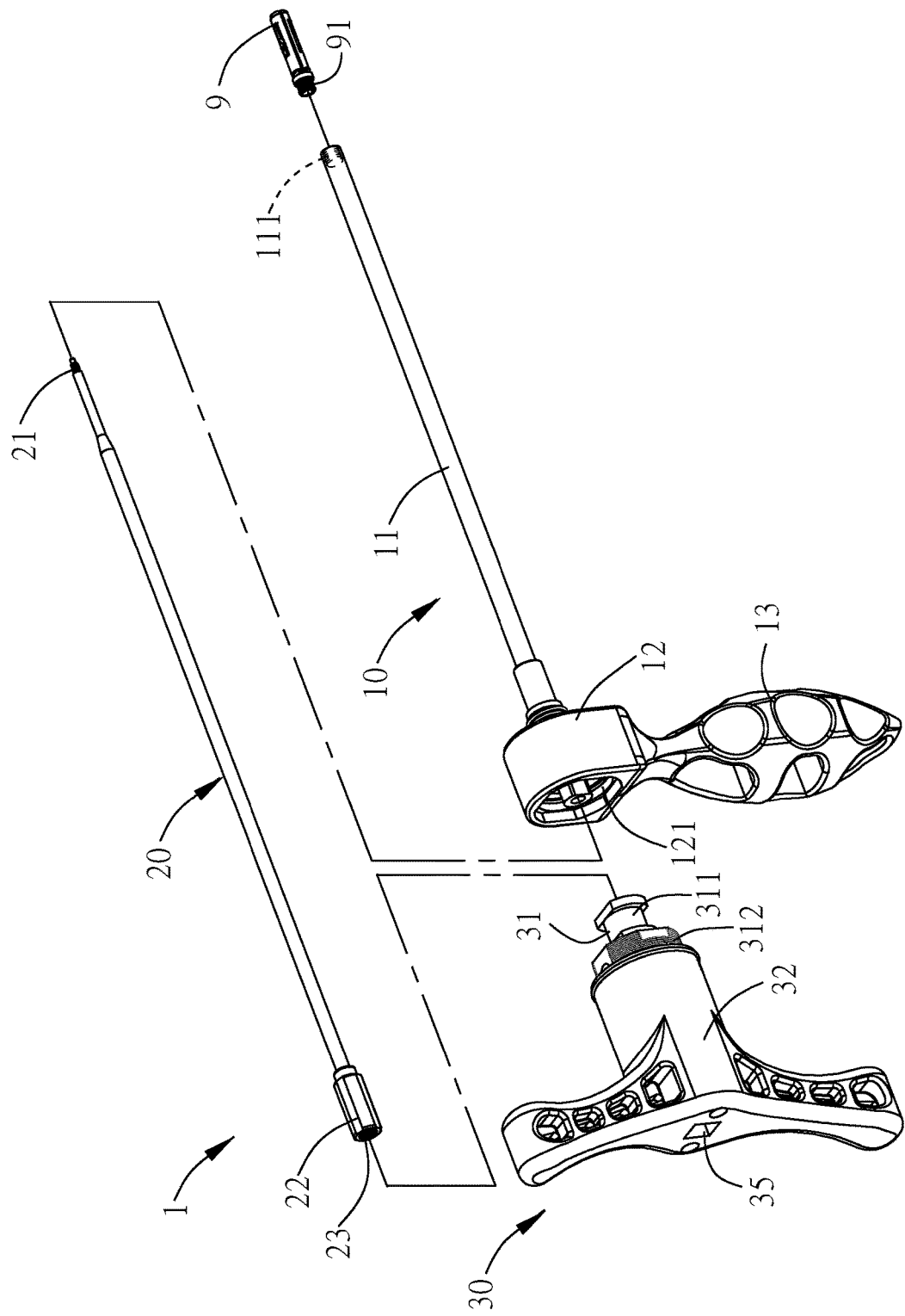
FIG. 3B is an exploded schematic diagram of a portion of the operating instrument shown in FIG. 2.
Figure 4:
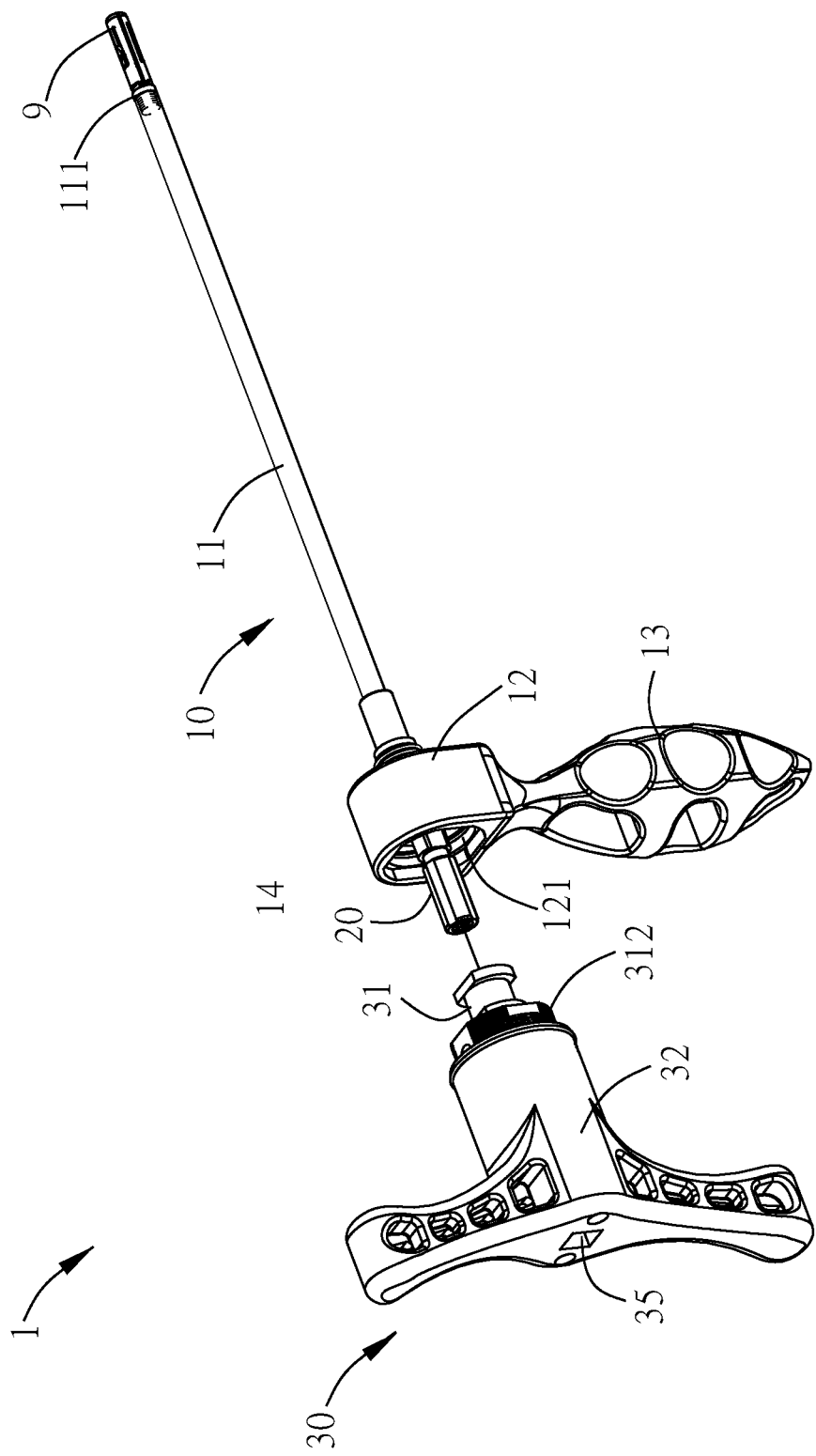
FIG. 4 is a schematic diagram of the central rod shown in FIG. 3 assembled with the extension assembly.
Figure 5:
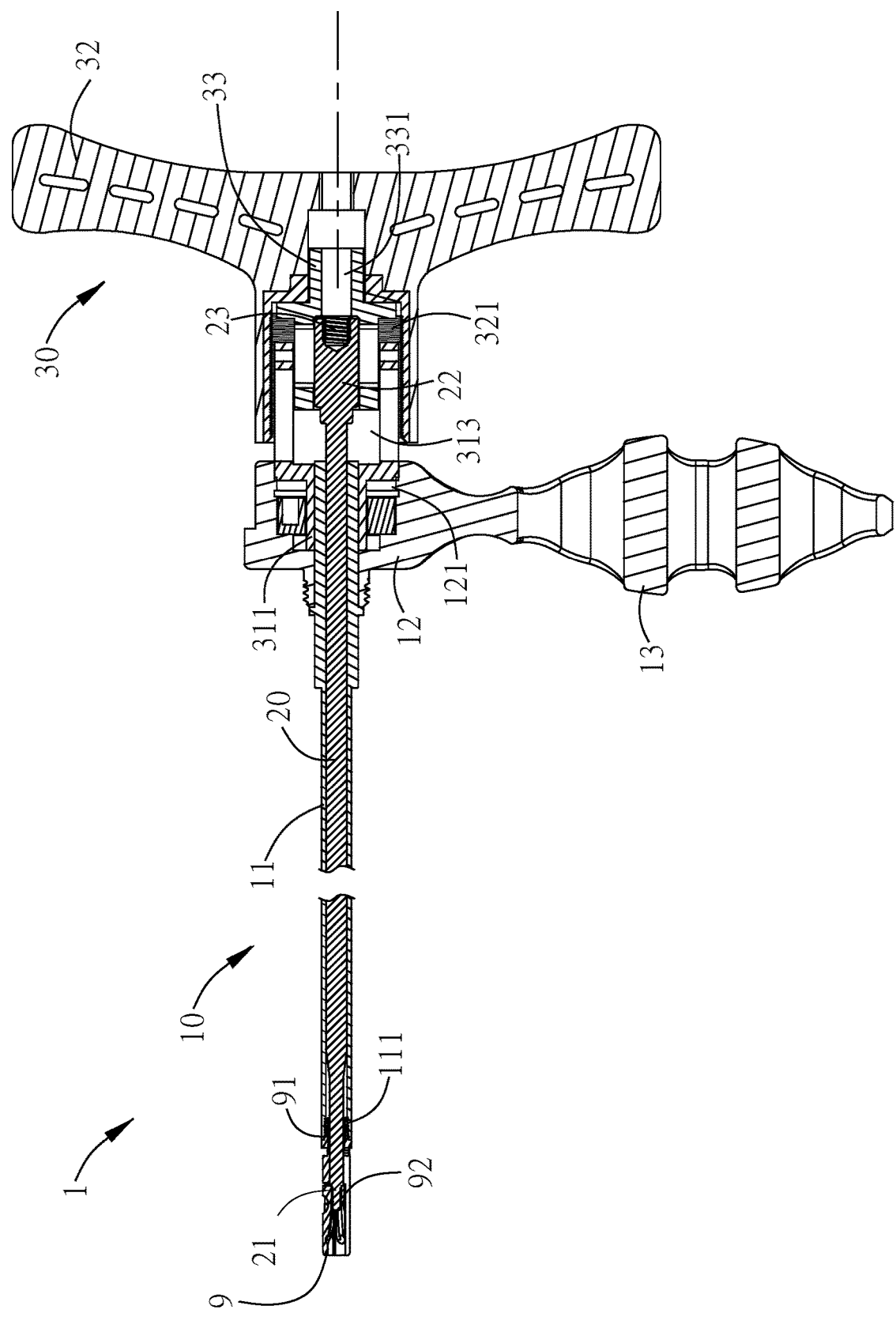
FIG. 5 is a schematic cross-sectional view of the operating instrument shown in FIG. 2.

Please refer to FIG. 2 to FIG. 5, where FIG. 2 is a schematic diagram of an embodiment of the operating instrument for a spinal implant of the present disclosure; FIG. 3A is an exploded schematic diagram of the extension assembly shown in FIG. 2; FIG. 3B is an exploded schematic diagram of a portion of the operating instrument shown in FIG. 2; FIG. 4 is a schematic diagram of the central rod shown in FIG. 3 assembled with the extension assembly; FIG. 5 is a schematic cross-sectional view of the operating instrument shown in FIG. 2. The operating instrument 1 of this embodiment is used in conjunction with the spinal implant 9 such that the surgeon or operator can hold the operating instrument 1 to manipulate, fix, move and place the spinal implant 9. The structural details of the spinal implant 9 can be referred to in the paragraphs of Related Art, and the detailed drawings can be referred to in FIGS. 1A and 1B. In this embodiment, the operating instrument 1 can be used to adjust the distance between the first part 91 and the second part 92 to adjust the degree of expansion of the spinal implant 9.

In this embodiment, the operating instrument 1 includes an extension assembly 10, a central rod 20, and an operating handle 30. The extension assembly 10 includes an outer sleeve 11, which has one end having a connecting portion 111, and the connecting portion 111 can be connected with the first part 91 of the spinal implant 9 by, for example, screw locking or mechanical interaction. The connecting portion 111 of this embodiment has an inner thread, and the first part 91 has an outer thread. The spinal implant 9 can be screwed to the connecting portion 111 of the extension assembly 10 to be fixed to the operating instrument 1. In other embodiments, the spinal implant 9 can also be fixed on the operating instrument 1 by engaging with the connecting portion 111.

The extension assembly 10 of this embodiment further includes a joining unit 12 and a gripping portion 13. As shown in FIG. 3A, the joining unit 12 is disposed at the end of the outer sleeve 11 opposite to the connecting portion 111, and the shape of the joining unit 12 is similar to a short cylindrical shape, with an opening 122 close to the bottom surface of the connecting portion 111. The opening 122 is a hole through which the outer sleeve 11 passes through the opening 122 to be combined with the joining unit 12. As shown in FIG. 3B, the joining unit 12 has a first accommodating groove 121 on the inside thereof. The gripping portion 13 is connected with the joining unit 12. The joining unit 12 and the gripping portion 13 may be integrally formed or may be two separate members connected by locking or snapping. When implanting the spinal implant 9, the surgeon holds the gripping portion 13 with one hand and screws the first part 91 of the spinal implant 9 into the connecting portion 111 of the outer sleeve 11 with the other hand, thereby fixing the spinal implant 9 to the extension assembly 10. Furthermore, the gripping portion 13 is not parallel to the outer sleeve 11. Preferably, an angle between the gripping portion 13 and the outer sleeve 11 may be between 80 degrees and 100 degrees, preferably 90 degrees; that is, the gripping portion 13 is preferably perpendicular to the outer sleeve 11 so that the surgeon can perform the implant surgery.

Please refer to FIG. 3B, wherein the central rod 20 is inserted into the outer sleeve 11. The length of the central rod 20 is longer than the total length of the outer sleeve 11 and the joining unit 12 such that the opposing first end 21 and second end 22 of the central rod 20 are exposed outside the outer sleeve 11 and the joining unit 12 respectively. During the insertion, the first end 21 of the central rod 20 is first inserted into the outer sleeve 11 from the side of the joining unit 12 and then protrudes out of the opposite side of the outer sleeve 11. In this embodiment, the first end 21 has an outer thread, and the inner side of the second part 92 of the spinal implant 9 is correspondingly disposed with an inner thread such that the first end 21 can be connected with the second part 92 in a screw-lock manner, as shown in FIG. 5. Finally, the operating handle 30 is sleeved on the first accommodating groove 121 and the second end 22 of the central rod 20 to be assembled with the central rod 20 and the joining unit 12. After it is assembled, the operator (such a surgeon) can control the movement of the central rod 20 through the operating handle 30 and adjust the expansion degree of the spinal implant 9.

Figure 6:
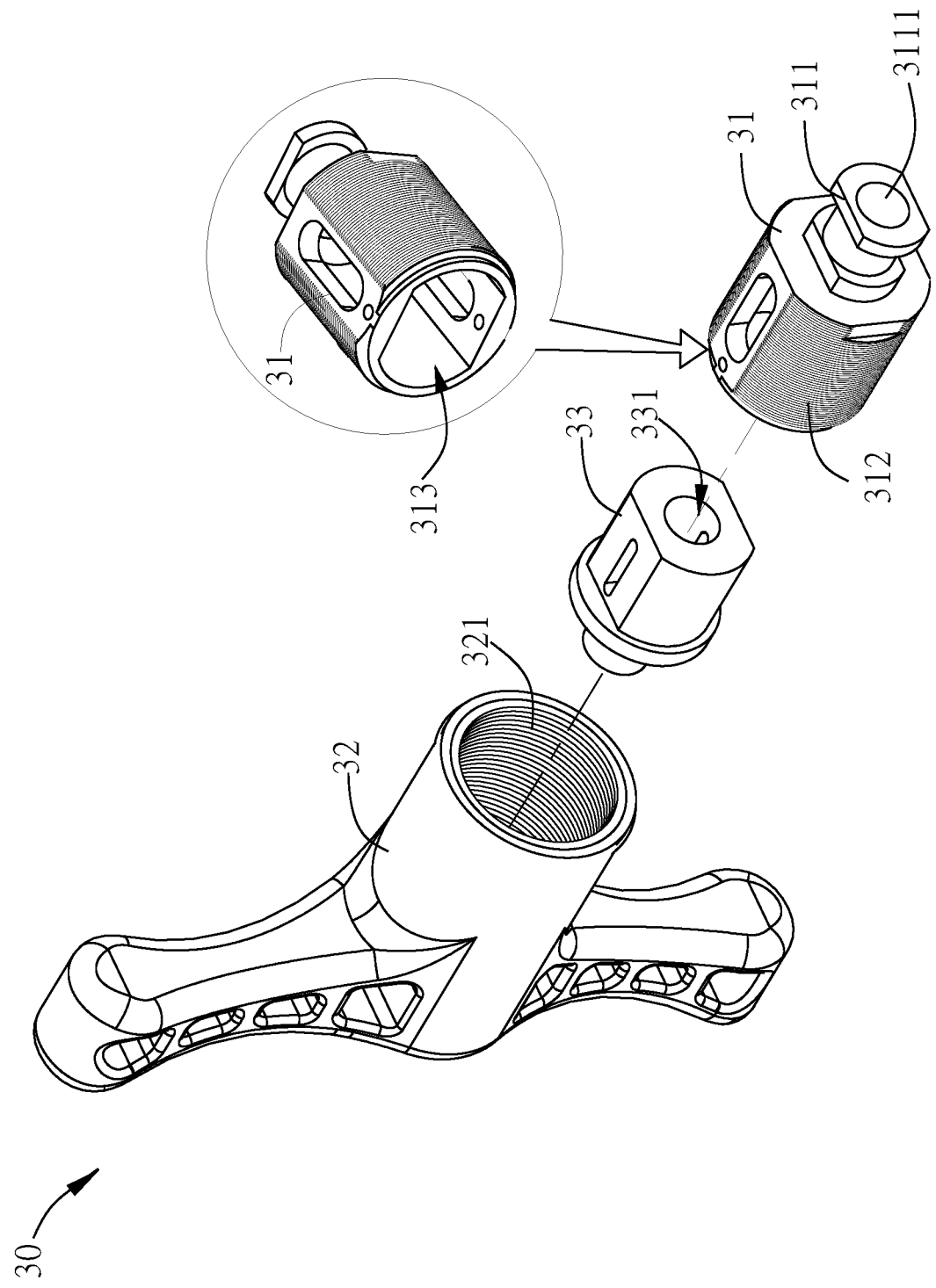
FIG. 6 is an exploded schematic diagram of the operating handle shown in FIG. 3B.

Now please refer to FIG. 6, which is an exploded schematic diagram of the operating handle shown in FIG. 3B. In this embodiment, the operating handle 30 includes a fixing element 31, a rotating element 32, and a pushing element 33. The front end of the fixing element 31 is connected with the joining unit 12. As shown in FIG. 5, a portion of the outer sleeve 11 is located in the first accommodating groove 121, and the fixing element 31 is not only inserted in the first accommodating groove 121 but also connected with the joining unit 12 and one end of the outer sleeve 11 opposite to the connecting portion 11l. The front end of the fixing element 31 has a pipe 311. The surgeon can hold the operating handle 30 and align the pipe 311 of the fixing element 31 with the first accommodating groove 121 to place the pipe 311 in the first accommodating groove 121 such that it is sleeved on the outside of the outer sleeve 11. With the aforementioned structure and combination, the fixing element 31 is fixed to the joining unit 12 and the outer sleeve 11 such that the relative position of the fixing element 31 and the outer sleeve 11 is fixed.

The fixing element 31 has an outer thread 312, and the rotating element 32 has an inner thread 321. The rotating element 32 is sleeved on the outside of the fixing element 31, and the inner thread 321 and the outer thread 312 correspond to each other such that the rotating element 32 can rotate relative to the fixing element 31 and move toward the extension assembly 10 along the thread.

The pushing element 33 is disposed between the fixing element 31 and the rotating element 32. In this embodiment, the fixing element 31 has a second accommodating groove 313, and the front end of the pushing element 33 is received in the second accommodating groove 313. The pipe 311 of the fixing element 31 has a through hole 3111, and the pushing element 33 has an assembly hole 331. After the two are assembled, the through hole 3111 is in communication with the assembly hole 331, thereby being in communication with the outer sleeve 11. When the fixing element 31 is assembled with the joining unit 12, the assembled fixing element 31 and the pushing element 33 are sleeved on the central rod 20 through the through hole 3111 and the assembly hole 331 together such that the second end 22 of the central rod 20 finally abuts against the limiting groove 332 at the bottom end of the assembly hole 331 (refer to FIG. 7). Since the bottom surface of the accommodating space inside the rotating element 32 abuts against the rear end of the pushing element 33, when the rotating element 32 is rotated to move forward, the rotating element 32 pushes the pushing element 33 to move forward, which in turn pushes the central rod 20 to move forward. It should be noted that the pushing element 33 is not fixed to the fixing element 31 or the rotating element 32; only the rear end of the pushing element 33 abuts against the bottom surface of the accommodating space inside the rotating element 32, so when the rotating element 32 is rotated, the pushing element 33 will not be driven to rotate but will only be pushed forward (in the direction of the extension assembly 10) by the rotating element 32 to move linearly. That is, the pushing element 33 does not rotate with the rotating element 32 but exhibits linear motion.

Figure 7:
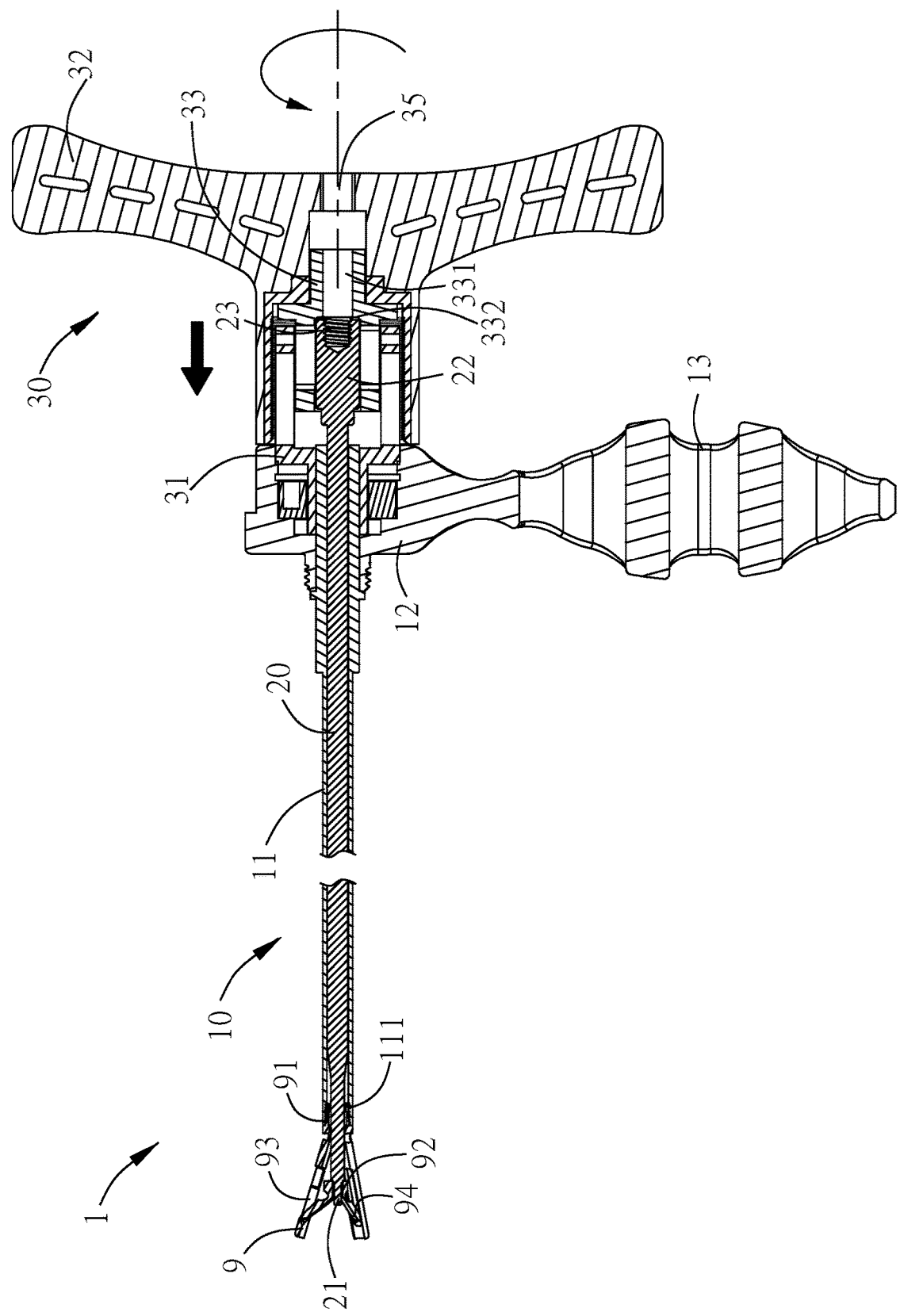
FIG. 7 is a schematic diagram of the operation of the operating instrument shown in FIG. 5.

FIG. 7 is a schematic diagram of the operation of the operating instrument shown in FIG. 5, wherein the spinal implant 9 shown in FIG. 5 has not been expanded by the operating instrument 1, and the spinal implant 9 shown in FIG. 7 has been expanded by the operating instrument 1. Please refer to FIG. 5 and FIG. 7 at the same time. The surgeon assembles the operating handle 30 with the extension assembly 10 and then rotates the rotating element 32 in a direction such as counterclockwise. When the rotating element 32 is rotated, the rotating element 32 can push the pushing element 33 to move along the long axis of the central rod 20 to drive the central rod 20 to drive the second part 92 of the spinal implant 9 to move, thereby changing the distance between the second part 92 and the first part 91 so as to expand the spinal implant 9. In detail, when the rotating element 32 is rotated, the rotating element 32 moves forward with respect to the fixing element 31 along the thread and drives the pushing element 33 to move forward, and in turn the pushing element 33 pushes the central rod 20 to move forward. Since the connecting portion 111 is connected with the first part 91 of the spinal implant 9 and the central rod 20 is connected with the second part 92 of the spinal implant 9, when the central rod 20 moves forward, the first part 91 is fixed, and the second part 92 is driven by the central rod 20 to move away from the first part 91, thereby increasing the distance between the first part 91 and the second part 92, as shown in FIG. 7.

The expansion arm 93 and the supporting arm 94 of this embodiment have multiple stress weakening points. When the distance between the first part 91 and the second part 92 increases, the expansion arm 93 and the supporting arm 94 are bent to make the spinal implant 9 expand. Specifically, one end of the expansion arm 93 is connected with the first part 91, and the connection has a stress weakening point. The other end of the expansion arm 93 is a free end, which is not connected with other elements. The expansion arm 93 has a supporting arm 94 disposed inside the expansion arm 93, and the supporting arm 94 is shaped like a tongue, which can be regarded as being cut from the expansion arm 93. One end of the supporting arm 94 is still connected with the inner side of the expansion arm 93 and is connected with a position close to the free end. The other end of the supporting arm 94 is connected with the second part 92. In this embodiment, the connection between the supporting arm 94 and the expansion arm 93 is designed with a stress weakening point, and the connection between the supporting arm 94 and the second part 92 is also designed with a stress weakening point. The stress weakening point is processed by thinning, hollowing, etc., such that the point is weaker than other adjacent parts, and the stress will be concentrated at this point when force is applied, causing the structure to deform. Among them, the two stress weakening points of the supporting arm 94 are formed by thinning the supporting arm in different directions. The stress weakening point connected with the second part 92 is a hemispherical concave structure, while the stress weakening point connected with the expansion arm 93 is an arc-shaped concave structure, and the opening directions of the two are opposite such that the supporting arm 94 can form a Z-shaped deformation after being stressed. When the distance between the first part 91 and the second part 92 increases, the supporting arm 94 will be stressed and bend at the stress weakening points, and then the expansion arm 93 will bend outward to achieve the expansion effect of the spinal implant 9, as shown in FIG. 7.

In addition, the number of expansion arms 93 can be three, and the expansion arms 93 can be designed as expansion arms of different sizes. Specifically, the size (for example, radian) of one expansion arm 93 is larger than the other two. This design can solve the problem of a spinal implant 9 having uniform expansion arms that are prone to deformation. When the spinal implant 9 is implanted into the implant channel in the vertebral body, the expansion arm 93 on the upper side (that is, the side closer to the patient's head) solely abuts against one side of the implant channel, and the two expansion arms 93 on the lower side (that is, the side closer to the patient's foot) are in contact with the other side of the implant channel. The upper expansion arm 93 (that is, the expansion arm that expands toward the patient's head) of the spinal implant 9 is the object that is mainly subjected to force. In the initial state of expansion, it will be affected by the force between the tissues and will easily bend and deform, or the expansion force will not be sufficient to overcome the stress between tissues. Therefore, the design of a larger upper expansion arm 93 allows the surgeon to align the expansion arm upward (that is, in the direction of the patient's head) during the operation and maintain this angle to implant the spinal implant 9. Since the upper expansion arm 93 has a large structural size, it has greater structural strength and supporting force, which can reduce deformation due to an insufficient load-bearing capacity.

After the spinal implant 9 is implanted in the affected part and expanded to restore the vertebral body, the central rod 20 is first removed, and then the distance between the first part 91 and the second part 93 is fixed with a fixing screw. Generally, the outer diameter of the fixing screw is smaller than the diameter of the first part 91 and smaller than the inner diameter of the second part 92 such that it can be inserted into the spinal implant 9 by other operating instruments, and the front end of the fixing screw can abut against the second part 92. Further, the first part 91 has an inner thread, and the fixing screw has a corresponding outer thread. When the fixing screw is screwed into the first part 91, the position of the fixing screw can be adjusted back and forth to fix the distance between the first part 91 and the second part 92. However, the degree of collapse of the vertebral body varies by cause, and the height of the required restoration varies with different physiological conditions of the patient. These factors will determine the height by which the spinal implant 9 needs to be expanded during the operation. When the expanded height of the spinal implant 9 is different, it means that the distance between the second part 92 and the first part 91 is different, so it needs to be matched with fixing screws of different lengths. Therefore, once the spinal implant 9 has been placed in the patient's body, an important issue is the method of determining the distance which the second part 92 has moved and selecting a fixing screw of the appropriate length.

In this embodiment, the linear distance moved by the rotating element 32 is substantially equal to both the moving distance of the central rod 20 and the distance between the first part 91 and the second part 92 when the spinal implant changes from the folded state to the expanded state. When the surgeon determines that the expanded height is sufficient, the surgeon can determine which fixing screw is to be used by indicating the linear distance which the rotating element 32 has moved (which is substantially equal to both the distance which the central rod 20 has moved and the distance which the second part 92 has moved relative to the first part 91).

Preferably, in different embodiments of the present disclosure, the operating handle 30 can have at least one movement marker 34, and the extension assembly 10 may include an indicator 14, wherein the movement marker 34 and/or the indicator 14 can be used by the surgeon to determine what distance the central rod 20 has moved or whether the central rod 20 has moved a predetermined distance.

Figure 8:
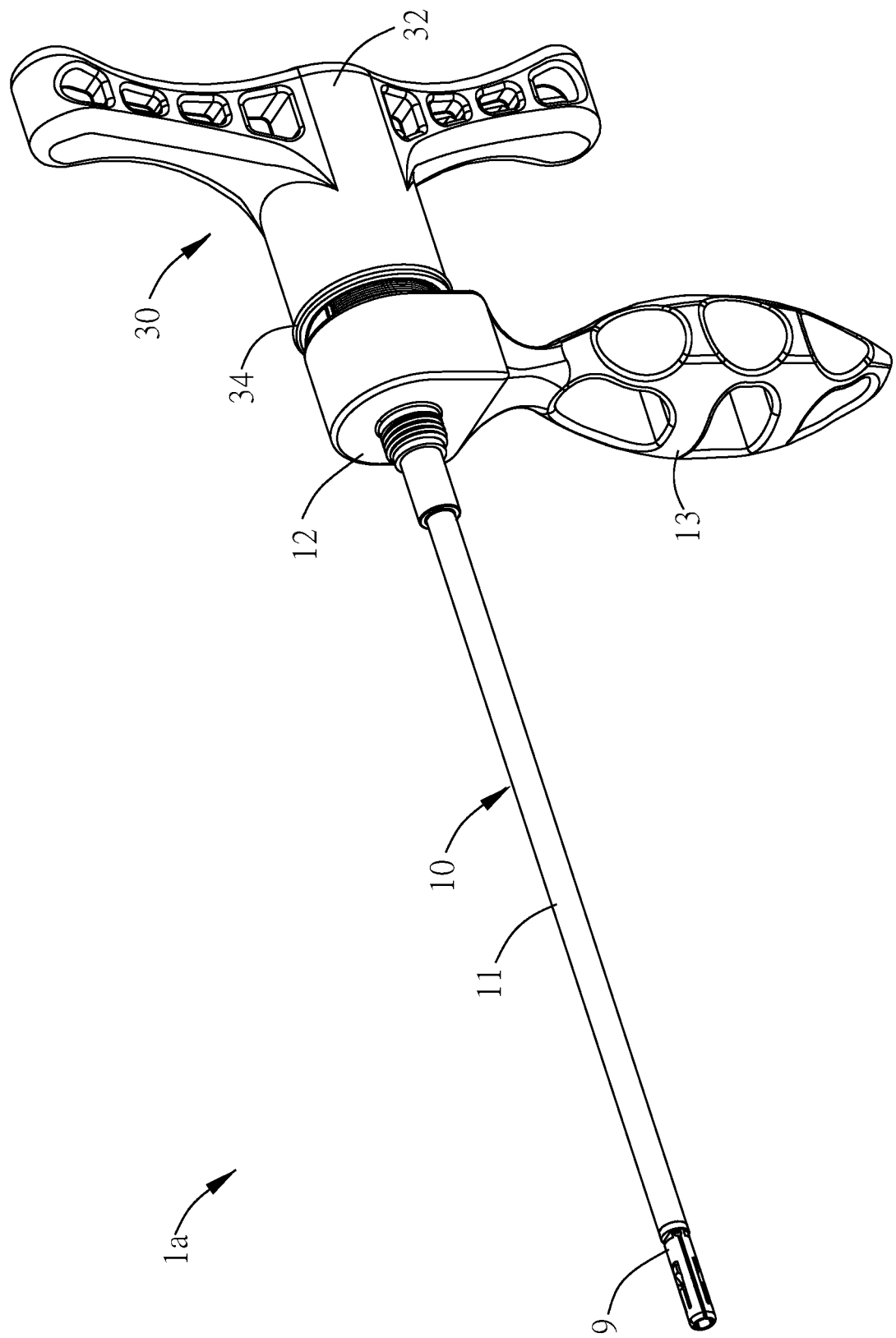
FIG. 8 is a schematic diagram of another embodiment of the operating instrument for a spinal implant of the present disclosure.

Please refer to FIG. 8, which is a schematic diagram of another embodiment of the operating instrument 1a for the spinal implant of the present disclosure. Preferably, in this embodiment, the operating handle 30 of the operating instrument 1a further includes a movement marker 34. The operating handle 30 is adjacent to the joining unit 12, and the movement marker 34 is disposed at one end of the operating handle 30 adjacent to the joining unit 12. The distance which the central rod 20/second part 92 has moved can be determined by the relative position change of the movement marker 34. In this embodiment, the movement marker 34 is disposed on the outside of the rotating element 32. Preferably, the movement marker 34 is a ring mark surrounding the rotating element 32. The forward moving distance of the movement marker 34 is equal to the distance which the central rod 20/second part 92 moves. Therefore, the distance which the central rod 20/second part 92 has moved can be judged by the relative distance between the movement marker 34 and the edge of the joining unit 12 so that a fixing screw of the corresponding length can be selected to maintain the distance between the first part 91 and the second part 92.

Figure 9:
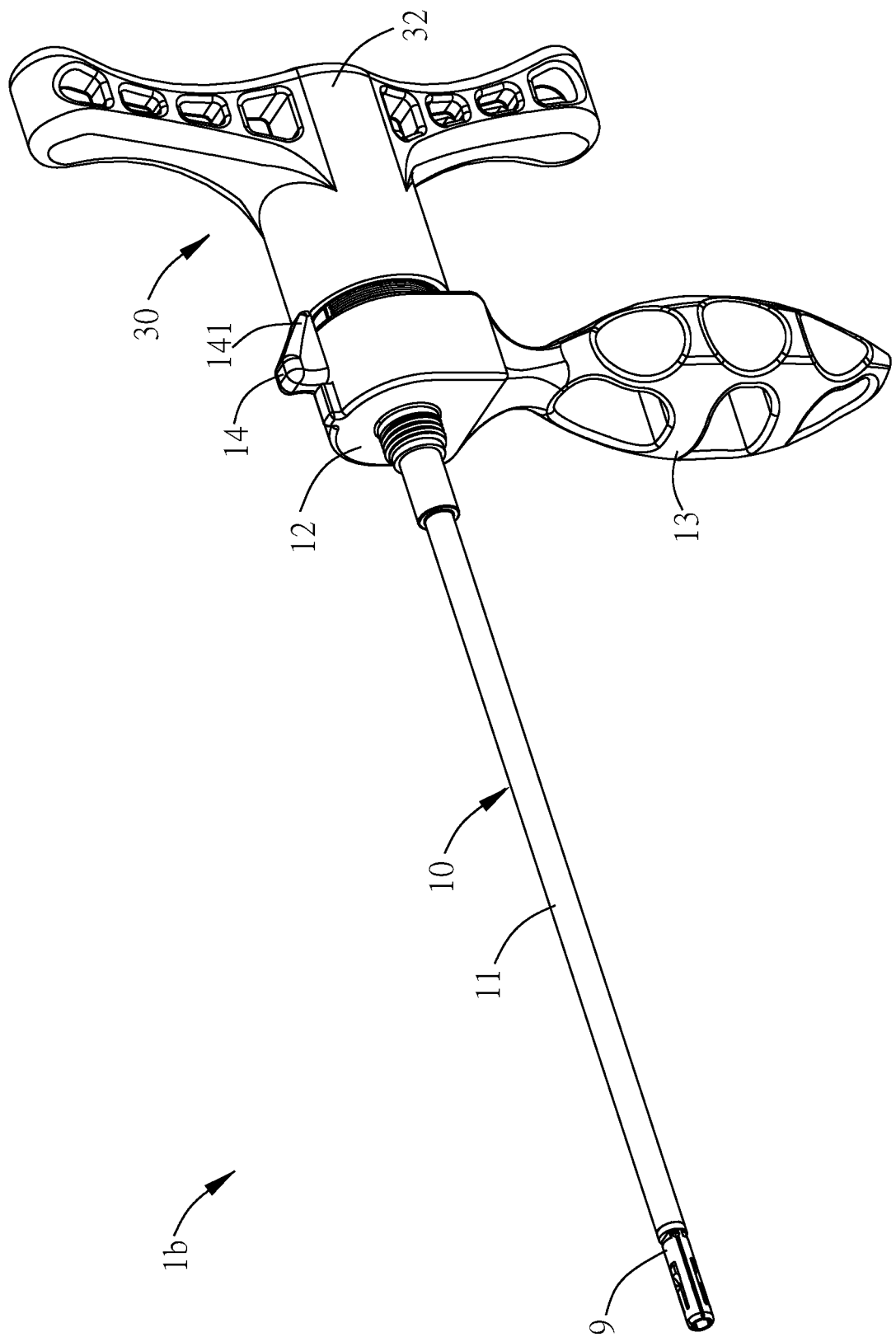
FIG. 9 is a schematic diagram of yet another embodiment of the operating instrument for a spinal implant of the present disclosure.

Please refer to FIG. 9, which is a schematic diagram of another embodiment of the operating instrument 1b for the spinal implant of the present disclosure. In this embodiment, the extension assembly 10 of the operating instrument 1b further includes an indicator 14. The indicator 14 is disposed on the outside of the joining unit 12, and the indicator 14 preferably has a tip 141, which extends from the joining unit 12 to the outside of the rotating element 32. Because the rotating element 32 changes its relative distance to the indicator 14 when it moves forward, the surgeon can determine the distance which the central rod 20/second part 92 has moved and then select a fixing screw of the corresponding length to maintain the distance between the first part 91 and the second part 92.

Figure 10A:
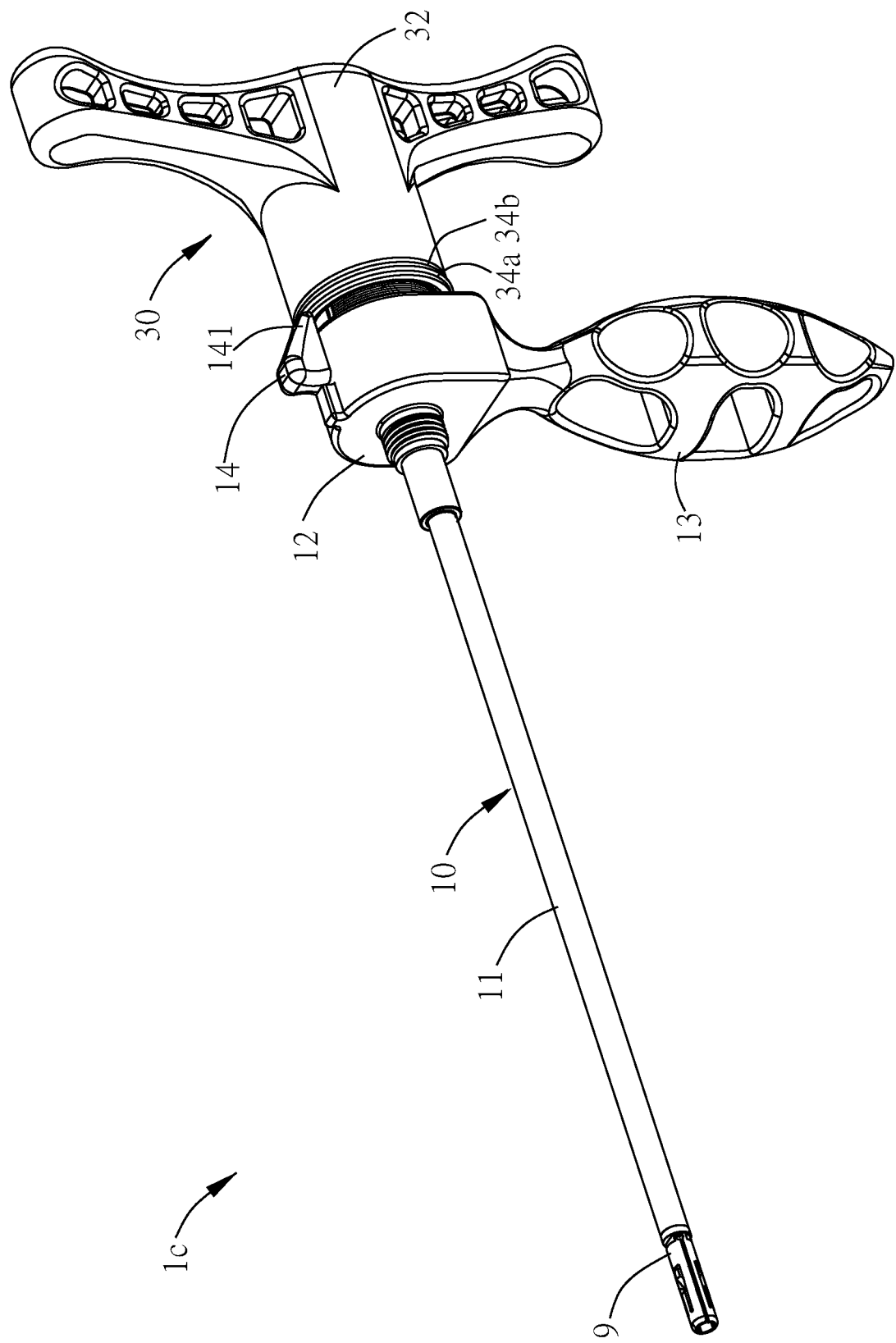
FIG. 10A is a schematic diagram of yet another embodiment of the operating instrument for a spinal implant of the present disclosure.
Figure 10B:
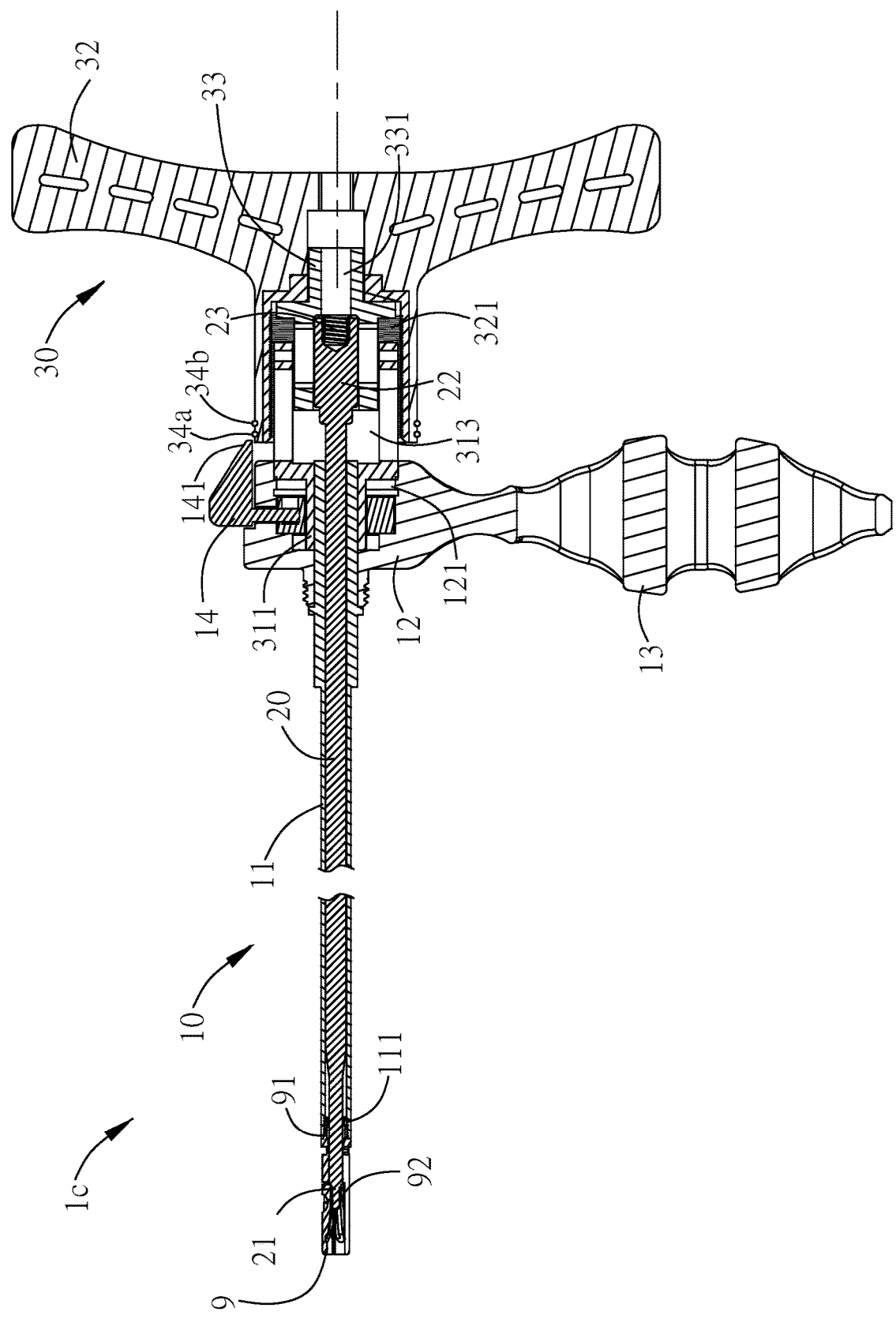
FIG. 10B is a schematic cross-sectional view of the spinal implant and operating instrument shown in FIG. 10A.
Figure 10C:
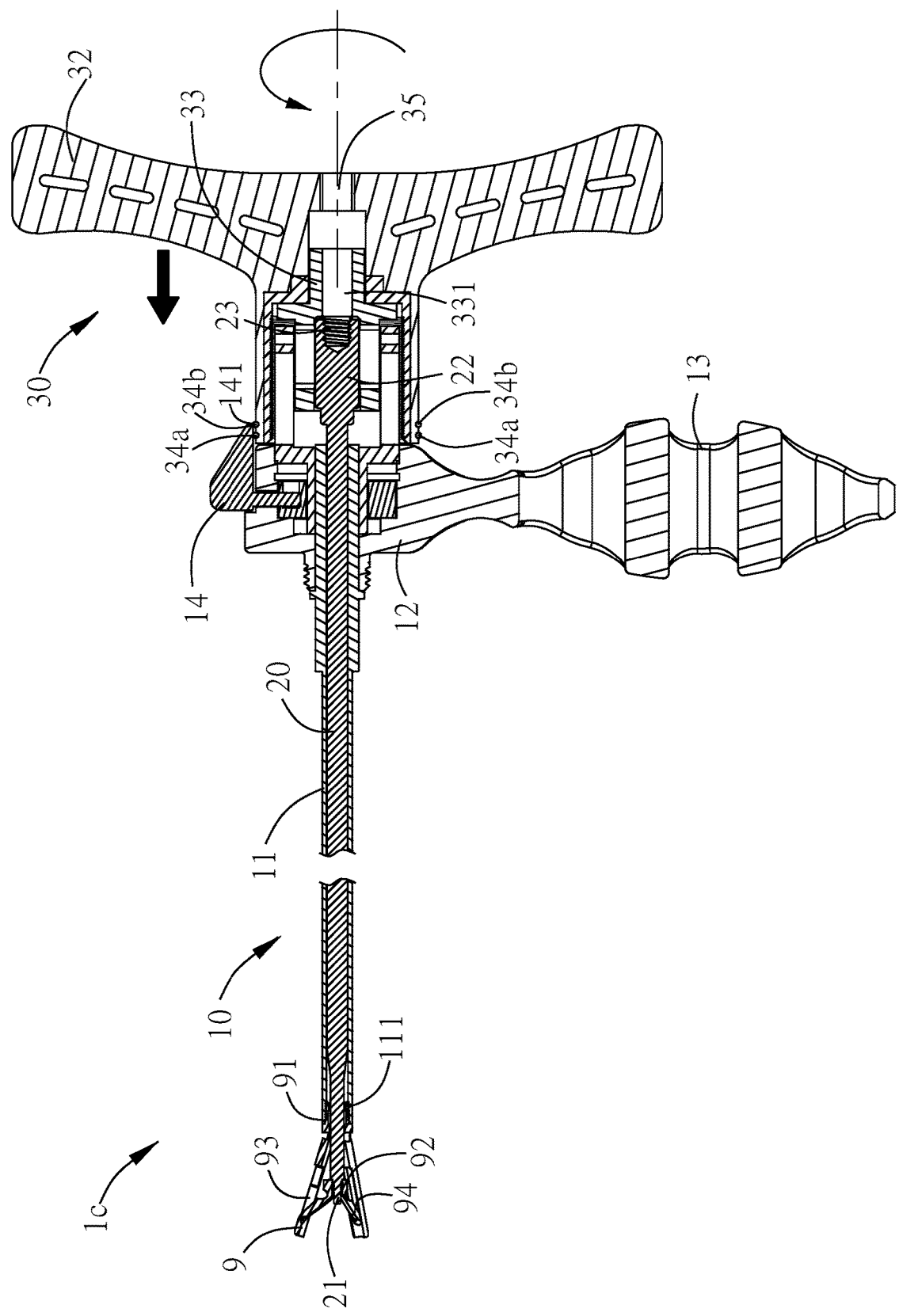
FIG. 10C is a schematic diagram of the operating instrument shown in FIG. 10B being driven to expand the spinal implant.

Please refer to FIG. 10A to 10C. FIG. 10A is a schematic diagram of yet another embodiment of the operating instrument for a spinal implant of the present disclosure. FIG. 10B is a schematic cross-sectional view of the spinal implant and operating instrument shown in FIG. 10A. This embodiment presents a preferred implementation. The operating handle 30 of the operating instrument 1c has a plurality of movement markers 34a, 34b, and an indicator 14 is provided on the outside of the joining unit 12. When the rotating element 32 is rotated, the movement markers 34a, 34b will gradually approach the tip 141 of the indicator 14, since the movement markers 34a, 34b represent the distance which the central rod 20/second part 92 has moved respectively (and also represent the distance which the second part 92 has been pushed), so the relative positions between the tip 141 and the movement markers 34a, 34b can be used for determining which fixing screw needs to be selected. As shown in FIG. 10B, the movement markers 34a and 34b are both ring-shaped markers surrounding the rotating element 32 in this embodiment. When the rotating element 32 and the central rod 20 do not move forward (that is, when the spinal implant 9 is not expanded), the tip 141 of the indicator 14 is disposed in front of the movement marker 34a. FIG. 10C is a schematic diagram of the operating instrument shown in FIG. 10B being driven to expand the spinal implant. When the rotating element 32 is rotated, the rotating element 32, the pushing element 33 and the central rod 20 all move along the long axis of the central rod 20 toward the spinal implant 9, and the position marker 34a or 34b gradually approaches the tip 141 of the indicator 14. When the tip 141 of the indicator 14 overlaps or does not reach the movement marker 34a, it means that the moving distance of the central rod 20/second part 92 is short. That is, the distance between the first part 91 and the second part 92 is short, and a short fixing screw, such as a fixing screw having a length of 23 mm, should be used. When the tip 141 of the indicator 14 overlaps the movement marker 34b or is disposed between the movement marker 34a and the movement marker 34b, it means that the central rod 20 has a long moving distance. That is, the distance between the first part 91 and the second part 92 is longer, and a longer fixing screw, such as a fixing screw having a length of 25 mm, should be used.

Figure 11:
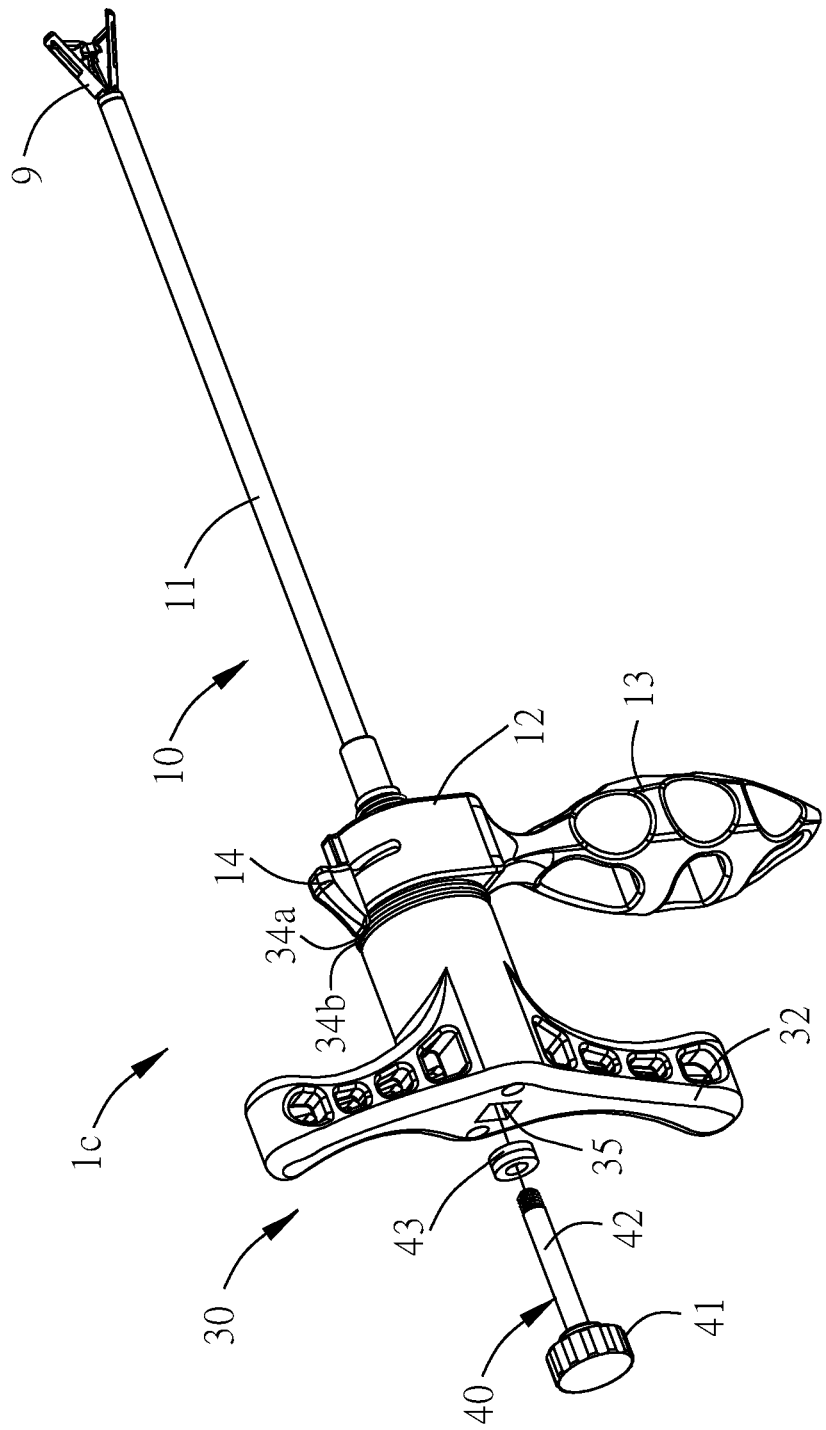
FIG. 11 is a schematic diagram of the operating instrument and its retracting element shown in FIG. 10A.
Figure 12:
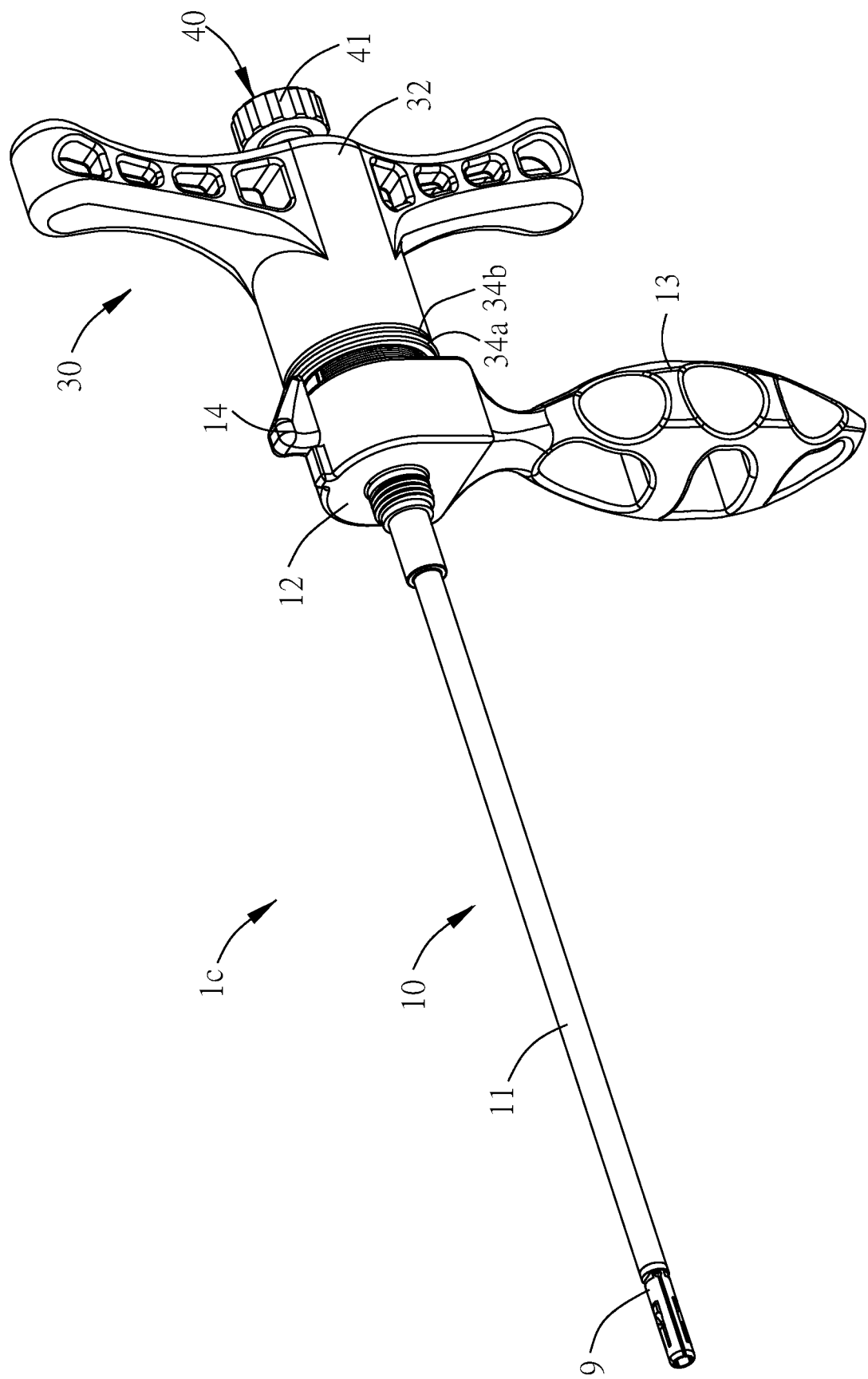
FIG. 12 is a schematic diagram of the retracting element shown in FIG. 11 being assembled with the operating handle and retracting.
Figure 13:
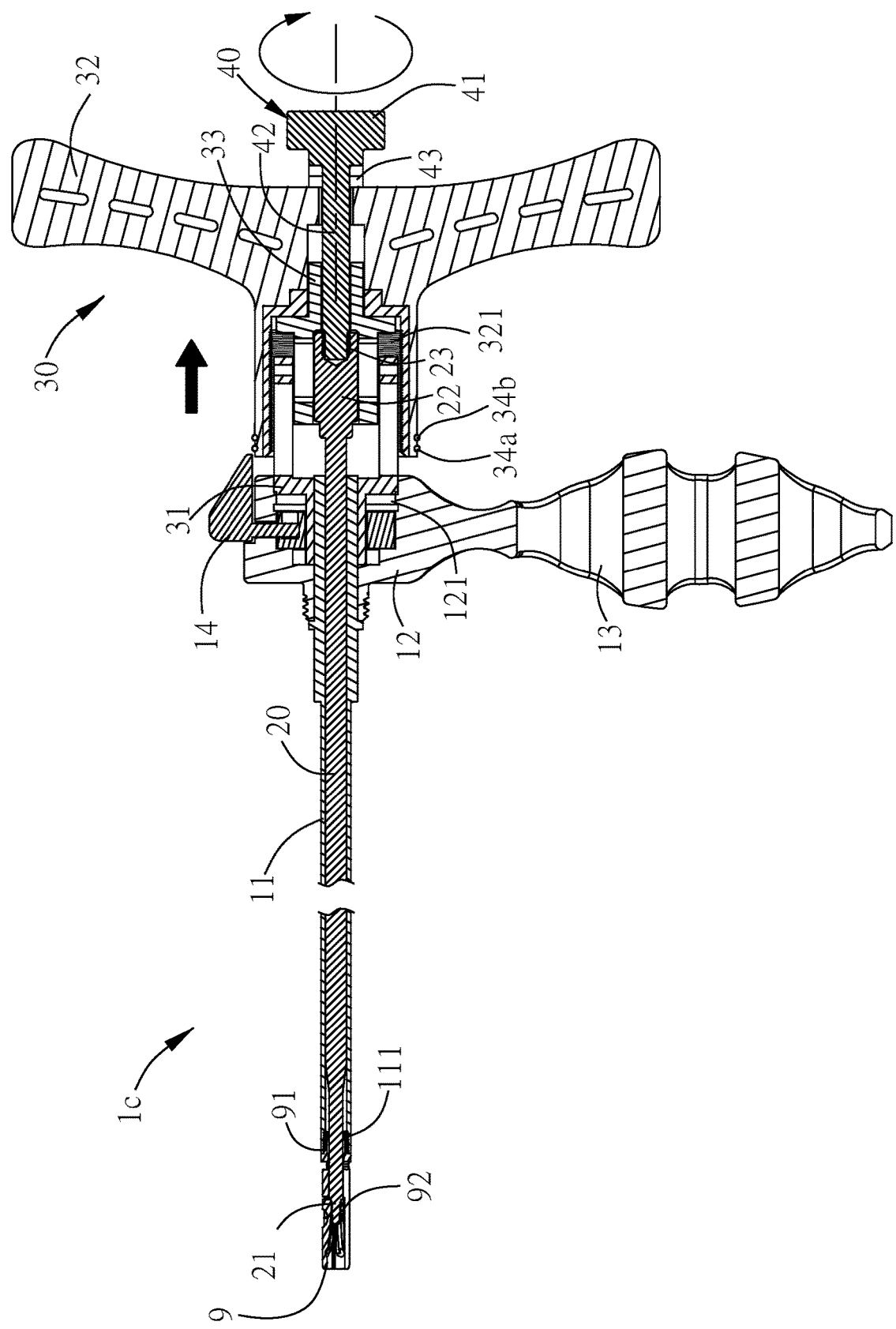
FIG. 13 is a schematic cross-sectional view of the operating instrument and retracting element shown in FIG. 12.

Please refer to FIG. 11 to 13. FIG. 11 is a schematic diagram of the operating instrument and its retracting element shown in FIG. 10A. FIG. 12 is a schematic diagram of the retracting element shown in FIG. 11 assembled with the operating handle and retracting. FIG. 13 is a schematic cross-sectional view of the operating instrument and retracting element shown in FIG. 12. During spinal surgery, if the implant path is shifted or the implant position is inappropriate, it is difficult to expand the spinal implant 9, or it could lead to slight deformation of the spinal implant 9. Therefore, the spinal implant 9 must be retracted and taken out. Preferably, the operating instrument 1c further includes a retracting element 40, which can be connected with the central rod 20 to pull the central rod 20 to move in the direction of the operating handle 30, thereby shortening the distance between the first part 91 and the second part 92 so that the spinal implant 9 can be retracted. Specifically, the pushing element 33 includes an assembly hole 331. The second end 22 of the central rod 20 has a fixing part 23. The fixing part 23 of this embodiment may be a screw hole so that the assembly hole 331 can be in communication with the fixing part 23. The retracting element 40 is mounted in the assembly hole 331 and engaged with the fixing part 23 of the central rod 20.

In this embodiment, the retracting element 40 is a retracting screw, which includes a nut 41 and a screw body 42. The operating handle 30 includes a through hole 35 located in the rotating element 32, and the through hole 35 is in communication with the assembly hole 331 (as shown in FIG. 11). When it is necessary to retract the expanded spinal implant 9, the surgeon can hold the retracting element 40 and align the screw body 42 with the through hole 35 such that the screw body 42 can be inserted into the through hole 35 and mounted in the assembly hole 331. The front end of the screw body 42 is locked into the fixing part 23 (screw hole), thereby connecting the retracting element 40 with the central rod 20. Further, the nut 41 is retained outside the operating handle 30; that is, on the outside of the rotating element 32 and the through hole 35.

Next, the surgeon can reversely rotate the rotating element 32, such as clockwise. When the rotating member 32 is reversely rotated, the outer surface of the rotating member 32 pushes against the nut 41 such that the retracting element 40 will move in the opposite direction along the long axis of the central rod 20; that is, it moves in the direction of the operating handle 30. Since the screw body 42 is connected with the central rod 20, the central rod 20 can be driven to drive the second part 92 to move in the opposite direction, thereby reducing the distance between the second part 92 and the first part 91 while retracting the spinal implant 9.

Preferably, the retracting element 40 further includes a washer 43 disposed between the rotating element 32 and the nut 41. The washer 43 can reduce the surface friction between the rotating element 32 and the nut 41, thereby preventing the nut 41 and the screw body 42 from rotating together due to friction when the rotating element 32 is rotated. In other words, when the surgeon rotates the rotating element 32 in the opposite direction, the nut 41 and the screw body 42 of the retracting element 40 can still move in a linear motion and will not rotate along with the rotating element 32.

Figure 14:
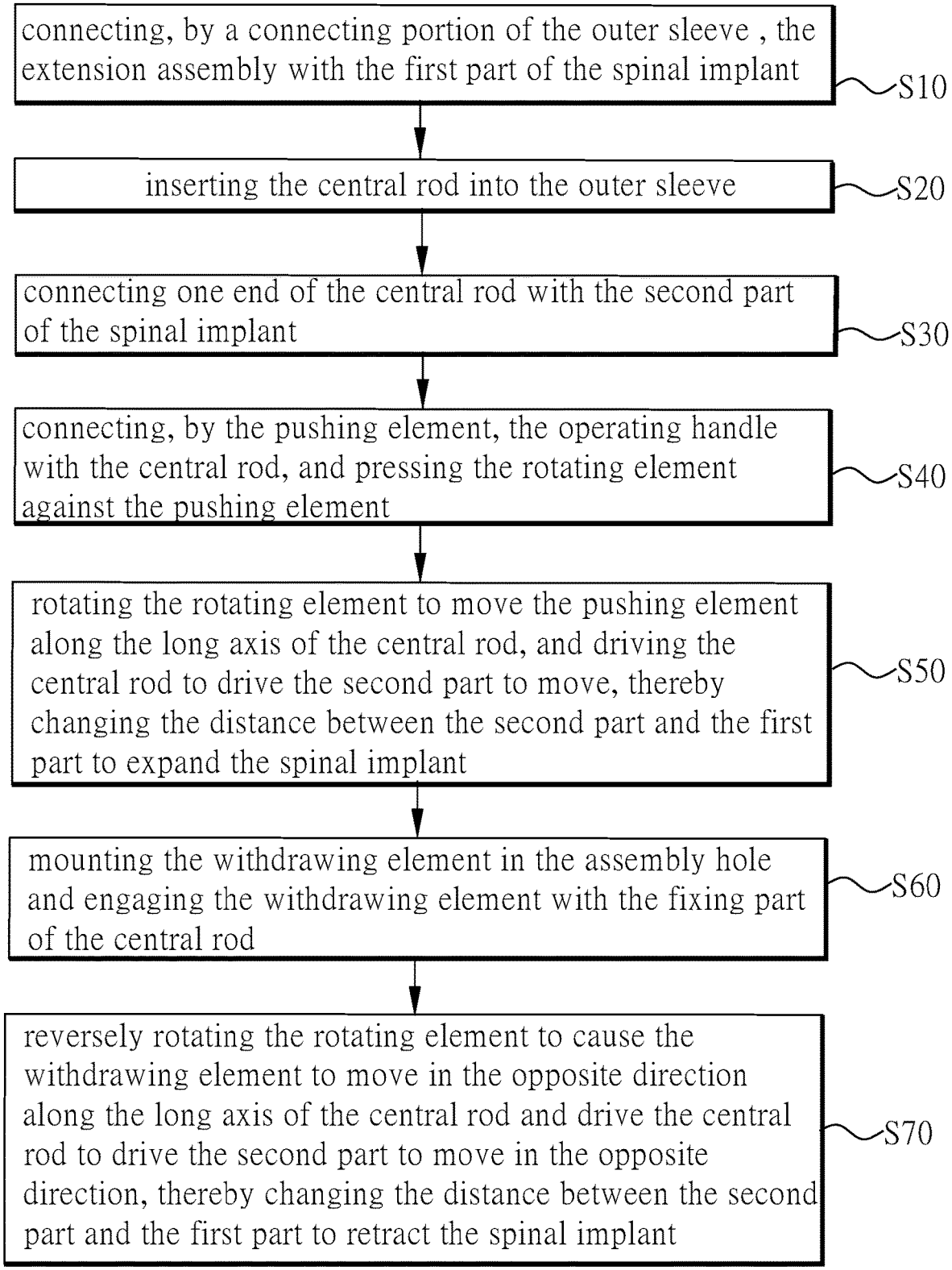
FIG. 14 is a schematic flowchart of an embodiment of the operating instrument for a spinal implant of the present disclosure.

Please refer to FIG. 14, which is a schematic flowchart of an embodiment of the operating instrument for a spinal implant of the present disclosure. The method of this embodiment is provided for operating the operating instrument 1 for the aforementioned spinal implant 9, which includes the following steps of: connecting, by a connecting portion 111 of the outer sleeve 11, the extension assembly 10 with the first part 91 of the spinal implant 9 (step S10); inserting the central rod 20 into the outer sleeve 11 (step S20); connecting one end of the central rod 20 with the second part 92 of the spinal implant 9 (step S30); connecting, by the pushing element 33, the operating handle 30 with the central rod 20, and pressing the rotating element 32 against the pushing element 33 (step S40); rotating the rotating element 32 to move the pushing element 33 along the long axis of the central rod 20, and driving the central rod 20 to drive the second part 92 to move, thereby changing the distance between the second part 92 and the first part 91 to expand the spinal implant 9 (step S50).

As mentioned above, the surgeon can first connect the outer sleeve 11 of the extension assembly 10 with the first part 91 of the spinal implant 9 (step S10, FIG. 3B) and then insert the central rod 20 into the outer sleeve 11 (step S20, FIG. 4) such that the front end of the central rod 20 is connected with the second part 92 of the spinal implant 9 (step S30, FIG. 5). Then the surgeon assembles the operating handle 30 with the extension assembly 10, connects the pushing element 33 with the central rod 20, and causes the rotating element 32 to abut against the pushing element 33 (step S40, FIG. 5). Finally, the rotating element 32 is rotated such that the pushing element 33 drives the central rod 20 to drive the second part 92 to move forward, thereby increasing the distance between the second part 92 and the first part 91 to expand the spinal implant 9 (step S50, FIG. 7).

Preferably, the operating instrument 1 of the present embodiment further includes a retracting mechanism (retracting element 40), and the operation method further includes the following steps of: mounting the retracting element 40 in the assembly hole 331 and engaging the retracting element 40 with the fixing part 23 of the central rod 20 (step S60), and reversely rotating the rotating element 32 to cause the retracting element 40 to move in the opposite direction along the long axis of the central rod 20 and drive the central rod to drive the second part 92 to move in the opposite direction, thereby changing the distance between the second part 92 and the first part 91 to retract the spinal implant 9 (step S70). In short, the retracting mechanism is for engaging the retracting element 40 with the central rod 20 (step S60, FIG. 12) and then rotating the rotating element 32 in the opposite direction to cause the retracting element 40 to move in the opposite direction along the long axis of the central rod 20, thereby reducing the distance between the second part 92 and the first part 91 for retraction of the spinal implant 9 (step S70, FIG. 13).

As described above, according to the operating instrument for the implant spinal of the present disclosure, the outer sleeve of the extension assembly is connected with the first part of the spinal implant, and the central rod is inserted into the outer sleeve and connected with the second part of the spinal implant. The operating handle has a fixing element, a rotating element and a pushing element. The inner thread of the rotating element corresponds to the outer thread of the fixing element, the pushing element is connected with the central rod, and the rotating element abuts against the pushing element. The surgeon needs only to rotate the rotating element, and the pushing element can drive the central rod to drive the second part to move, thereby changing the distance between the second part and the first part so as to expand the spinal implant. Therefore, the operating instrument of the present disclosure enables the surgeon to precisely control the moving distance of the second part so as to carefully adjust the degree of expansion of the spinal implant to achieve a better treatment effect.

In addition, the mechanism of the operating instrument allows the retracting element to be assembled on the operating handle so as to be connected with the central rod, thereby controlling the movement of the second part. When the retracting element is assembled, the surgeon needs only to reversely rotate the rotating element to cause the pushing element to drive the central rod to enable the second part to move in the opposite direction, thereby changing the distance between the second part and the first part to retract the spinal implant. In this way, the present disclosure can solve the problems of the spinal implant possibly being implanted improperly and needing to be taken out and re-inserted again, or the degree of expansion being too large and needing to be reduced, among other issues.

It should be noted that the described embodiments are only for illustrative and exemplary purposes and that various changes and modifications may be made to the described embodiments without departing from the scope of the application as disposed by the appended claims.

What is claimed is:

1. An operating instrument for a spinal implant, the spinal implant comprising a first part and a second part, the operating instrument comprising:
an extension assembly comprising:
an outer sleeve, wherein one end of the outer sleeve has a connecting portion connected with the first part of the spinal implant;
a central rod inserted into the outer sleeve, the central rod having a first end and a second end opposite to each other, the first end being connected with the second part of the spinal implant, the second end having a fixing part;
an operating handle comprising:
a fixing element having an outer thread;
a rotating element having an inner thread, wherein the rotating element is sleeved on the outside of the fixing element, and the inner thread and the outer thread correspond to each other; and
a pushing element connected with the second end of the central rod, the rotating element being pressed against the pushing element, wherein the rotating element is rotated to cause the pushing element to move along the long axis of the central rod, and the central rod is driven to drive the second part to move, thereby changing the distance between the second part and the first part so as to expand the spinal implant, the pushing element comprising an assembly hole, the assembly hole in communication with the fixing part; and
a retracting element mounted in the assembly hole and engaged with the fixing part of the central rod.

2. The operating instrument as claimed in claim 1, wherein the retracting element is a retracting screw comprising a nut and a screw body, the operating handle comprises a through hole located in the rotating element, and the through hole is in communication with the assembly hole; the screw body is inserted into the through hole to be mounted in the assembly hole, and the nut is retained outside of the operating handle.

3. The operating instrument as claimed in claim 2, wherein when the rotating element is reversely rotated so as to cause the retracting element to move in an opposite direction along the long axis of the central rod, the central rod is driven to drive the second part to move in the opposite direction, thereby changing the distance between the second part and the first part for retraction of the spinal implant.

4. The operating instrument as claimed in claim 2, wherein the retracting element further comprises a washer disposed between the rotating element and the nut.

5. The operating instrument as claimed in claim 1, wherein the extension assembly further comprises a joining unit connecting the fixing element with one end of the outer sleeve opposite to the connecting portion.

6. The operating instrument as claimed in claim 5, wherein the operating handle is adjacent to the joining unit, the operating handle has at least one movement marker, and the movement marker is disposed on the side of the operating handle close to the joining unit.

7. The operating instrument as claimed in claim 6, wherein the extension assembly further comprises an indicator, and the indicator indicates the moving distance of the central rod.

8. The operating instrument as claimed in claim 7, wherein the indicator is disposed on an outside of the joining unit and has a tip, the movement marker is disposed on one end of the rotating element adjacent to the joining unit, and the tip extends from the joining unit to an outside of the rotating element.

9. The operating instrument as claimed in claim 8, wherein the operating handle comprises a plurality of the movement markers, and the rotating element is rotated to move the tip to overlap with one of the movement markers.

10. The operating instrument as claimed in claim 5, wherein the extension assembly further comprises a gripping portion connected with the joining unit, and the gripping portion is not parallel to the outer sleeve.

11. The operating instrument as claimed in claim 5, wherein the joining unit has a first accommodating groove, and a portion of the outer sleeve is accommodated in the first accommodating groove; a front end of the fixing element has a pipe, and the pipe is accommodated in the first accommodating groove and sleeved on the outside of the outer sleeve.

12. The operating instrument as claimed in claim 1, wherein the fixing element has a second accommodating groove and is in communication with the outer sleeve, and the second end of the central rod and a portion of the pushing element are accommodated in the second accommodating groove.

* * * * *